(12) United States Patent
Gowey

(10) Patent No.: US 10,758,578 B2
(45) Date of Patent: Sep. 1, 2020

(54) HERBAL FORMULATIONS OF CARNIVOROUS PLANTS AND METHODS FOR TREATING INFLAMMATION

(71) Applicant: GOWEY RESEARCH GROUP, PLLC, Flagstaff, AZ (US)

(72) Inventor: Brandie Gowey, Flagstaff, AZ (US)

(73) Assignee: GOWEY RESEARCH GROUP PLLC, Flagstaff, AZ (US)

( * ) Notice: Subject to any disclaimer, the term of this patent is extended or adjusted under 35 U.S.C. 154(b) by 998 days.

(21) Appl. No.: 14/990,107

(22) Filed: Jan. 7, 2016

(65) Prior Publication Data

US 2017/0112885 A1 Apr. 27, 2017

Related U.S. Application Data

(63) Continuation-in-part of application No. 13/309,144, filed on Dec. 1, 2011, now abandoned, and a continuation-in-part of application No. 14/305,933, filed on Jun. 16, 2014, now abandoned, and a continuation-in-part of application No. 14/306,581, filed on Jun. 17, 2014, now abandoned.

(60) Provisional application No. 61/448,824, filed on Mar. 3, 2011, provisional application No. 61/418,692, filed on Dec. 1, 2010, provisional application No. 61/835,741, filed on Jun. 17, 2013, provisional application No. 61/835,749, filed on Jun. 17, 2013.

(51) Int. Cl.
| | |
|---|---|
| *A61K 36/185* | (2006.01) |
| *A61K 38/05* | (2006.01) |
| *A61K 9/00* | (2006.01) |
| *A61K 45/06* | (2006.01) |
| *A61K 31/7008* | (2006.01) |
| *A61K 31/07* | (2006.01) |
| *A61K 31/59* | (2006.01) |
| *A61K 31/198* | (2006.01) |
| *A61K 31/519* | (2006.01) |
| *A61P 29/00* | (2006.01) |

(52) U.S. Cl.
CPC .......... *A61K 36/185* (2013.01); *A61K 9/0019* (2013.01); *A61K 31/07* (2013.01); *A61K 31/198* (2013.01); *A61K 31/519* (2013.01); *A61K 31/59* (2013.01); *A61K 31/7008* (2013.01); *A61K 38/05* (2013.01); *A61K 45/06* (2013.01); *A61P 29/00* (2018.01)

(58) Field of Classification Search
None
See application file for complete search history.

(56) References Cited

U.S. PATENT DOCUMENTS

| | | | |
|---|---|---|---|
| 4,104,373 A | 8/1978 | Sichert | |
| 5,925,364 A | 7/1999 | Ribier et al. | |
| 6,559,182 B1 | 5/2003 | Purcell | |
| 7,964,354 B2 | 6/2011 | Ferguson et al. | |
| 8,445,198 B2 | 5/2013 | Knudsen | |
| 2006/0240092 A1 | 10/2006 | Breitenkamp | |
| 2007/0122492 A1* | 5/2007 | Behr | A61Q 17/04 424/725 |
| 2008/0182245 A1 | 7/2008 | Brown et al. | |
| 2008/0199420 A1 | 8/2008 | Wendel et al. | |
| 2008/0311167 A1 | 12/2008 | Oronsky et al. | |
| 2009/0004302 A1 | 1/2009 | Cyr | |
| 2009/0253601 A1 | 10/2009 | Tan et al. | |
| 2010/0216865 A1 | 8/2010 | Elias | |
| 2012/0141610 A1 | 6/2012 | Gowey | |
| 2013/0143945 A1 | 6/2013 | Brown | |

FOREIGN PATENT DOCUMENTS

EP 0555691 B1 10/1998

OTHER PUBLICATIONS

What is Prolotherapy Treatment for Chronic Back Pain? 2007 (https://www.spine-health.com/treatment/injections/what-prolotherapy-treatment-chronic-back-pain).*
Sarapin, 2011, https://web.archive.org/web/20101204134909/https://www.drugs.com/drp/sarapin.html.*
Mesquita et al., Anti-inflammatory effect of dietary supplementation with omega-3 fatty acids in rats, 2011, Rev. Dor. Sao Paulo, 12: 337-41.*
Rahman, Inflammation and the Regulation of Glutathione Level in Lun g Epithelial Cells, 1999, Antioxidants & Redox Signaling, 1: 425-447.*
Medicalnewstoday, 2017, https://www.medicalnewstoday.com/articles/248423.php.*
Martin-Sanchez et al. (2009) Pain Medicine vol. 10, No. 8, 1353-1368.
Comelli et al. (2008) Phytother. Res. 22, 1017-1024.
Harris et al. (2012) BMC Complementary and Alternative Medicine, 12:245.
Manchikanti et al. (2004) Pain Physician 7:59-62.
Novak et al. (2001) Flavour Fragr. J. 16: 259-262.
Oomah et al. (2002) Food Chemistry 76: 33-43.
Ross et al. (1996) J. Nat. Prod. 59: 49-51.
Russo et al. (2003) Psychopharmacology 165: 431-432.
John Brittnacher, International Carnivorous Plant Society, http://www.carnivorousplants.org.
Science Finder session began Nov. 7, 2015 at 10:10 am.
Muhammad et al., Antidiabetic Compounds from Sarracenia purpurea Used Traditionally by the Eeyou Istchee Cree First Nation, 2012, J Nat Prod, 75: 1284-1288.

(Continued)

*Primary Examiner* — Terry A McKelvey
*Assistant Examiner* — Catheryne Chen
(74) *Attorney, Agent, or Firm* — Nguyen Tarbet

(57) ABSTRACT

Formulations and methods for treating inflammation using pitcher plants. The pitcher plant is made into herbal preparations, such as tinctures and infused solutions. The herbal preparation of the pitcher plant is combined with glutathione, solutions, supplements, or other plant preparations to make a composition. Administering the composition to a subject can reduce inflammation, increase fibroblast growth factors, and adjust fibrinogen to homeostatic levels, thereby treating the inflammation.

12 Claims, 1 Drawing Sheet

(56) References Cited

OTHER PUBLICATIONS

Hensen et al. "Flesh-eating plants". Discover: Science for the curious (Oct. 2001), pp. 1-9. Retrieved fromL <URL: http://discovermagazine.com/2001/oct/featplants>.

Truth in Aging Web Publication Date: 2006. Retrieved from the Internet: <URL: http://www.truthinaging.com/ingredients/ammonium-acryloyldimethyltaurate>.

Dermis Web Publication Date: 2006. Retrived from the Internet: <URL: http://orgs.dermis.net/content/e05eecdrg/e05news/e686/e706/index_ger.html>.

PCCA Web Publication Date: 2007 <URL: http://www.customcompounding.com.au/wpcontent/uploads/2012/03/VERSABASE-INGREDIENTS.pdf>.

Shrewsbury, R. "Compounding Facilities and Equipment" from Applied Pharmaceutics in Contemporary Compounding: 2nd Edition (2008), pp. 29 and 31-33.

Mody et al. "Isolation of the Insect Paralyzing Agent Coniine from Sarracenia flava". Experientia 32/7 (1976), pp. 829-830.

Preparation of Supposiories. Internet Archive Date: Dec. 11, 2008 [Retrieved from the Internet on: Mar. 24, 2015] . . . Retrieved from the Internet: <URL:https://web.archive.org/web/20081211055237/http://pharmlabs.unc.edu/labs/suppository/bases.html>.

Pharmaceutical Compounding and dispensing by John F Marriott, et.al of chapter 5 (Extemporaneous dispersing), p. 66.

Yang et al. Oncotarget 8: 72835-72846, 2017.

Hall et al. Cell Death and Disease 7m e2184, 1-14, 2016.

Song et al. Cell Research 23: 274-289, 2013.

Jee et al. Brain 135: 1237-1252, 2012.

* cited by examiner

HERBAL FORMULATIONS OF CARNIVOROUS PLANTS AND METHODS FOR TREATING INFLAMMATION

CROSS-REFERENCE

This application claims priority to U.S. patent application Ser. No. 13/309,144, filed on Dec. 1, 2011, which is a non-provisional of U.S. Provisional Patent Application No. 61/418,692, filed Dec. 1, 2010, and U.S. Provisional Patent Application No. 61/448,824, filed Mar. 3, 2011, the specification(s) of which is/are incorporated herein in their entirety by reference.

This application claims priority to U.S. patent application Ser. No. 14/305,933, filed on Jun. 16, 2014, which is a non-provisional of U.S. Provisional Patent Application No. 61/835,741, filed Jun. 17, 2013, the specification(s) of which is/are incorporated herein in their entirety by reference.

This application claims priority to U.S. patent application Ser. No. 14/306,581, filed on Jun. 17, 2014, which is a non-provisional of U.S. Provisional Patent Application No. 61/835,749, filed Jun. 17, 2013, the specification(s) of which is/are incorporated herein in their entirety by reference.

FIELD OF THE INVENTION

The present invention features formulations and methods of treatment using herbal formulations containing carnivorous plants, in particular, pitcher plants such as *Sarracenia flava* and *Sarracenia purpurea*.

BACKGROUND OF THE INVENTION

Historical data on uses of the pitcher plant spp. (i.e. *Sarracenia* spp.) demonstrate efficacy as a digestive aid and anti-viral (webmd.com, http://www.ncbi.nlm.nih.gov/pmc/articles/PMC3302891/), having been employed as a medicine in early pharmacies, but never studied as to the exact effect on the immune system. However, work done on the present invention has identified that the carnivorous plant(s), *Sarracenia flava* and *Sarracenia purpurea* (pitcher plant) and mixed hybrids or related species thereof, have the capability to decrease and stabilize fibrinogen levels, and do so quite dramatically.

Fibrinogen is a precursor acute-phase reactant protein produced by the liver in response to signals of systemic circulating cytokines, possibly as an effort to stimulate a healing reaction within the immune system. It is involved in the creation of clots, atherosclerosis, and generalized inflammation. In the systemic circulation, it gets converted to fibrin, which the present invention has determined can be homeostatically used by fibroblast and myofibroblast cells to heal or build tissues. Excess fibrinogen increases inflammation, cancer and over-deposition of tissues, such as scar tissues. Fibroblast and myofibroblast activities are regulated by proteins called fibroblast growth factors (FGF), of which there are 23 identified currently (Mueller and Fusenig 2011 and Baird and Klagsbrun 1991). These growth factors are dependent on the presence of glutathione, which are found within the growth factors.

SUMMARY

The present invention features a composition comprising an herbal preparation of carnivorous plants, such as pitcher plants. It is surprisingly discovered that the present composition is effective against diseases that manifest as a result of the deleterious effects of inflammation and cancerous cells.

During the course of the invention, it was discovered that current lab "normals" for fibrinogen may indeed be flawed. For example, some labs set lab normals as 193-507 mg/dL and physicians read that as saying the clotting pathways are normal and working fine, and below 193 mg/dL means the patient will start to bleed out. Without wishing to limit the invention to a particular theory or mechanism, the present invention has determined that fibrinogen is healthy and ideal when levels are within 165-225 mg/dL, which is defined herein as "homeostatic levels", in order for the patient to live free of inflammatory symptoms. This range can be reached when pitcher plant preparations of the present invention are administered orally. Above 225 mg/dL indicates that the patient may be struggling with a systemic inflammatory process or cancer. For example, tumors tend to start developing once the fibrinogen levels surpass 225 mg/dL. Fibrinogen levels over 225 and into the 300 s and above can create excess fibrin, which the body can use to make scar tissue. This fibrin may also be in the tissues of any disease, i.e. cancer, autoimmune conditions, blockages, etc.

During the course of the invention, it was revealed that fibrinogen levels may be sensitive and can rapidly increase from exposure to small amounts of stress or even processed sugars in the diet. Each of these patients also struggled with inflammatory or cancer-related conditions including, but not limited to, multiple sclerosis, arthritis, cancer, or autoimmune conditions. It is possible that the body can manufacture fibrinogen immediately should the need arise, such as for clotting. Moreover, it is a possibility that people may suffer from medical concerns because their fibroblasts are constantly responding to circulating inflammation, which means that these fibroblasts cells are constantly trying to keep other cells and tissues healthy.

Like fibrinogen, fibroblast growth factors (FGF) have lab normals that are currently not established, and are insignificant if they appear on the lab. There are 23 known growth factors that can signal cells what tissue to heal or maintain. The growth factors are dependent on glutathione and must have vitamins A and D and magnesium in the extracellular matrix around them in order to signal cells to heal.

Currently, FGF-23 is the only one that can be checked in conventional labs, its range being 44-215 Ru/mL. Without wishing to limit the present invention to a particular theory or mechanism, the present invention has found that FGF-23 levels below 99 Ru/mL indicate that the patient is a "slow healer". The patient is chronically sick and does not improve easily despite receiving treatments such as chemotherapy and common neutraceuticals. Chronic diseases are likely to develop and set in to the patient. Further, the patient does not get well overall and tends to stay sick, and may likely need medication, surgery, etc. FGF-23 levels from 100-199 Ru/mL indicate that the patient is a "fast healer". FGF-23 levels above 200 could indicate a health condition such as cancer or acute inflammatory conditions. At these levels, the body is trying to heal something but is unable to do so.

Current medical standards classify high FGF-23 levels to be harmful because the increase in fibroblast growth factors can signify that a disease or disorder, such as cancer, is secreting them to proliferate. In the case of cancer, since the tumors produce fibroblast growth factors as the cell is dying, an oncologist would attempt to decrease glutathione, thereby decreasing and inhibiting fibroblast growth factors production in order to inhibit the tumors. It has been surprisingly discovered that these current medical standards are wrong.

Without wishing to limit the invention to a particular theory or mechanism, the present invention has surprising discovered that the body is increasing FGFs in an effort to heal. It is believed that the disease is producing what it needs to stimulate healing, yet current medical practices attempt to inhibit this. For example, by increasing fibroblast growth factors production, the tumors can shrink and heal. The composition of the present invention is capable of increasing FGF levels via administering injections of a composition of the present invention, and decreasing fibrinogen levels to homeostatic conditions via administering oral composition of the present invention, thereby treating the disease. Clearly, current medical practices teach away from the concept of increasing fibroblast growth factors production as taught in the present invention.

Immune cells, or lymph cells, can circulate within the body in a rhythm. Fibroblasts cells can be found in the lymph fluid. Current medical standards teach that minimal blood supply or lack thereof in blood flow to the tissue may be the reason for why the tissue does not heal well. Without wishing to limit the invention to a particular theory or mechanism, the present invention reasons that if there were a lack of blood flow to the tissue, then the fibroblast is collecting in the vicinity of the tissue. Hence, it is another objective of the present invention to stimulate fibroblast movement in order to promote healing of the tissue. For example, administering topical compositions of the present invention can stimulate movement of the fibroblast, as well as transport nutrients to the FGF and the fibroblast extracellular matrix.

According to one embodiment, the present invention features compositions and methods of treating inflammation. The method may comprise administering one or more injections of a therapeutically effective amount of a composition to fascia and ligaments surrounding a spine of the subject. The composition may comprise an herbal preparation of a carnivorous plant, such as a pitcher plant *Sarracenia purpurea*, at a range of about 1% to 99% volume of the composition, and a glutathione at a range of about 1% to 99% volume of the composition. The herbal preparation of the carnivorous plant is effective for facilitating transmission of the glutathione to fibroblast growth factors. Moreover, the administering of the composition to the subject can increase fibroblast growth factors at measureable levels in the subject, and adjusts fibrinogen levels to homeostatic levels in the subject, thereby ameliorating symptoms of the inflammation of the subject. Furthermore, the one or more injections are effective for stimulating movement and activity of fibroblast cells via insertion of the injection needle (http://www.ncbi.nlm.nih.gov/pubmed/24593827). The composition may further comprise supplements such magnesium, vitamin D, vitamin A, and glucosamine.

According to another embodiment, the present invention features oral compositions and methods for decreasing fibrinogen levels to homeostatic levels. The oral compositions may comprise the herbal preparation of the carnivorous plant, such as the pitcher plant *Sarracenia purpurea*. Patients, when orally administered the composition, see a resolution of inflammatory symptoms via a decrease in fibrinogen levels measureable in blood. Without wishing to limit the present invention to particular mechanism or theory, the pitcher plant is surprisingly discovered to decrease fibrinogen levels to homeostatic levels, as shown by pre- and post-patient labs upon prescribed oral use of the pitcher plant, thereby reducing symptoms of inflammation due to the decrease in fibrinogen levels, and increasing pain-relieving effects.

In yet a further embodiment, the present invention features topical compositions comprising the herbal preparation of the carnivorous plant, such as the pitcher plant *Sarracenia flava*. Without wishing to limit the present invention to particular mechanism or theory, the pitcher plant is surprisingly discovered to stimulate movement of fibroblasts. Moreover, the pitcher plant has a transdermal effect, i.e. the pitcher plant is amphiphilic such that it can carry substances, such as magnesium, which is insoluble in fats, into and through the skin.

It is known that botanicals and nutraceuticals (supplements) have synergistic effects when combined together, for example with regards to the use of Chinese herbs (Xu et al. 2014 and Yang et al. 2009). According to embodiments of the present invention, the composition can be combined with antioxidants such as berries or glutathione, fibroblast protectors such as extracts of orchids, fibroblast motility enhancers such as extracts of lily, immune modulators such as curcumin or black cohosh extracts, and cytoprotectors such as astragalus. The pitcher plant may also be combined with bases such as DMSO (dimethylsulfate, jacoblab.com) or coconut oil, cleansers such as lye for saponification processes, and astringents such as witch hazel.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

DESCRIPTION OF PREFERRED EMBODIMENTS

Figure 1:
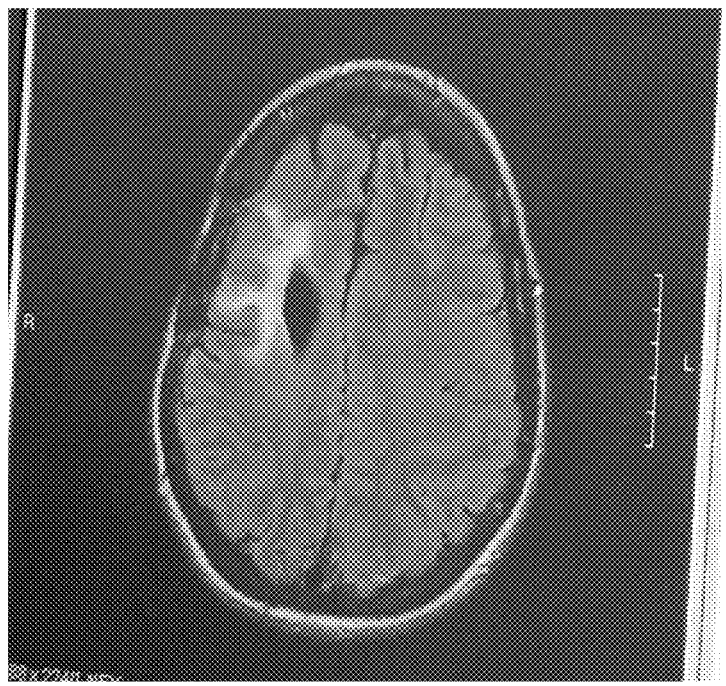
FIG. 1 shows an MRI image of a brain. The white-colored portion of the brain indicates cancer.

According to the International Carnivorous Plant Society (www.carnivorousplants.org), a "carnivorous plant" is a predatory plant that obtains its nutrients by trapping and killing prey. A carnivorous plant has the following features: 1. the plant captures and fills prey; 2. the plant has some mechanism to digest the prey; and 3. the plant absorbs the nutrients from the prey. Some non-limiting examples of carnivorous plants include plants from the genus *Sarracenia, Dionaea, Utricularia*, and *Drosera*. The preferred carnivorous plants of the present invention are pitcher plants, namely, *Sarracenia flava* and *Sarracenia purpurea*.

As used herein, the term "extract" is defined as a separation of the beneficial (medicinal) components of an herb from the fibrous, less useful part of the plant. Extracts can be in a liquid or powdered form.

As used herein, the term "infuse" is defined as a procedure of withdrawing nutritive compounds of an herb into a medium, and allowing them to linger in the medium for a period of time to allow for the transfer of herbal extracts into the medium. An "infused solution" is the resulting solution with the nutritive compounds.

As used herein, the term "tincture" is defined as a heavily concentrated extract made by placing chopped fresh or dried herbs into a container and covering them with a solvent. The mixture is then sealed and allowed to macerate for several weeks.

As used herein, an "herbal preparation" or a "plant preparation" may be an extract, tincture, or infused solution made or prepared from an herb or plant. The herbal preparation contains the active components from the herb or plant. For example, the herbal preparation of a pitcher plant may be a pitcher plant extract, tincture, or infused solution. A pitcher plant component is extracted from the pitcher plant. As used herein, a "pitcher plant component", or alternatively, an "active component" is defined as the beneficial (medicinal) plant parts/material of pitcher plant. For instance, the herbal preparation of the pitcher plant may be an oil infused with the pitcher plant active component.

As a non-limiting example of extracting the active components from the pitcher plant, in some embodiments, the pitcher plant is cut into small pieces, pulverized, mashed, or chopped. The pitcher plant pieces are placed in a non-reactive storage container, such as glass or plastic. A required amount of liquid, such as water, alcohol, or vinegar, is added to the storage container. The mixture is set aside and allowed to incubate for a period of time. The pitcher plant's active components transfer from the plant material into the liquid. After the incubation period is over, any plant material solids are separated from the liquid. The resulting liquid is the pitcher plant tincture. In another embodiment, a pitcher plant extract is prepared by dehydrating the pitcher plant material and pulverizing or grinding the plant material into a powder.

As used herein, the term "supplement" are generally understood include, but are not limited to, vitamins, minerals, fiber, fatty acids, amino acids and amine derivatives. As used herein, the term "minerals" may be categorized into two kinds of minerals: macrominerals and trace minerals. Macrominerals include, but are not limited to, calcium, phosphorus, magnesium, sodium, potassium, chloride and sulfur. Trace minerals include, but are not limited to, iron, manganese, copper, iodine, zinc, cobalt, fluoride and selenium. Examples of vitamins include, but are not limited to, retinoic acid (Vitamin A), vitamin B-complex, vitamin C, vitamin D, vitamin E, and vitamin K. Non-limiting examples of fatty acids include phosphocholine, phosphytidylcholine, and phosphytidylserine. Non-limiting examples of amino acids include cysteine and arginine, such as L-arginine. Examples of amine derivatives include, but are not limited to, glucosamine.

As used herein, "inflammation" is a biological protective response in which the body attempts to remove harmful stimuli, including, damaged cells, irritants, or pathogens, in order to begin the healing process. Inflammation is a component or symptom of numerous diseases and conditions, including but not limited to, cancer, arthritis such as osteoarthritis and osteoporosis, diabetes herniated discs, lesions such as brain lesions, skin lesions, wounds, ulcers, tumors, and sores, skin disorders such as eczema, gastrointestinal disorders such as irritable bowel syndrome, psychological disorders such as depression and anxiety, and cognitive decline such as Alzheimer's and dementia. Symptoms of inflammation include pain, heat, redness, swelling, scar tissue, and loss of function.

As used herein, the terms "administering" or "administer" is defined as the introduction of a substance (composition) into cells in vitro or into the body of an individual in vivo and includes topical, oral, nasal, ocular, rectal, vaginal and parenteral routes. The composition of the present invention may be administered via any route of administration, including but not limited to topical, subcutaneous, intramuscular, intravenous, intradermal, or orally. For example, the composition can be administered by needle injections into the fascia and ligaments surrounding the spine. As known to one of ordinary skill in the art, ligaments are fibrous bands of connective tissue that attach to bone. For example, the supraspinous ligament is a ligament that attaches the tip of each spinous process to the other. The spinous process is a bony projection off the posterior (back) of each vertebra. Other examples of ligaments include the nuchal ligament, which is a ligament at the back of the neck that is continuous with the supraspinous ligament, and the interspinous ligaments, which are ligaments that join the spinous processes along their adjacent borders. As known to one of ordinary skill in the art, the fascia is a strong sheath-like connective tissue. For example, the thoraco-lumbar fascia, or lumbodorsal fascia, is a tough, membranous connective tissue covering the muscles of the back of the trunk. In the lumbar region, the lumbodorsal fascia is attached, medially, to the spinous processes of the thoracic vertebrae.

As defined herein, the terms "treating" or "treatment" of a condition includes: (1) preventing the condition, i.e., causing the clinical symptoms of the condition not to develop in a mammal that may be exposed to or predisposed to the condition but does not yet experience or display symptoms of the condition; (2) inhibiting the condition, i.e., arresting or reducing the development of the condition or its clinical symptoms; or (3) ameliorating or relieving the condition, i.e., causing regression of the condition or its clinical symptoms. The composition can be administered to treat inflammation. As used herein, the terms "treat" or "treatment" refer to both therapeutic treatment or preventative measures, wherein the object is to prevent or slow down (lessen) an undesired physiological change or disorder, such as the development or worsening of inflammation. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., any disease or condition that results in inflammation) prior to administration of the composition of the invention.

As used herein, Cytenssic means "cell essence, and Cytenssic therapy is a treatment developed in the present invention. The principle of Cytenssic therapy is that the body is able to heal itself via the fibroblast growth factors, and any other related growth factor. The base formulation of Cytenssic therapy is the carnivorous plant and glutathione. Minerals, vitamins, and other anti-cancer herbs can be added to the base formulation. When the FGF levels are increased, inflammation is reduced and the body is able to heal and rid itself of the disease.

As used herein, the term "therapeutically effective amount" refers to an amount of a compound, i.e. the composition, effective to treat a condition, disease or disorder in a subject. In the case of inflammation, the therapeutically effective amount of the present composition may reduce (i.e., slow to some extent and preferably stop)

inflammation, and/or relieve, to some extent, one or more of the symptoms associated with a disorder or disease. The "therapeutically effective amount" will vary depending on the compound, the condition and its severity and body factors such as age, weight, etc., of the subject to be treated.

As used herein, the term "homeostasis", and derivatives thereof, refers to the ability to regulate variables such that conditions remain stable and relatively constant. For instance, when fibrinogen levels are at homeostasis, the levels are within the healthy range of 165-225 mg/dL, and maintained in that range, as discovered in the present invention.

As used herein, a "solution" is defined as is a homogeneous mixture composed of two or more substances. A "solute" is a substance dissolved in another substance, known as a "solvent".

As used herein, the terms "those defined above" and "those defined herein" when referring to a variable incorporates by reference the broad definition of the variable as well as any narrow and/or preferred, more preferred and most preferred definitions, if any.

Preparing Pitcher Plant Tincture

In preferred embodiments, the herbal preparation of carnivorous plant is prepared from pitcher plant, such as a *Sarracenia purpurea* or a *Sarracenia flava* plant. In alternative embodiments, a tincture may be obtained from other carnivorous plant tinctures. Some non-limiting examples of carnivorous plants are the *Drosera* species, *Dionaea* species, and the *Utricularia* species.

A pitcher plant tincture is made using a "soak and press" technique. As a non-limiting example, the pitcher plant tincture may be made from a *Sarracenia purpurea* (pitcher plant). The *Sarracenia purpurea* material is obtained, preferably from plants grown in the absence of pesticides, and then chopped, forming a "chopped plant mixture". The material may be the leaves, i.e. pitchers, of the plant. In some embodiments, during the harvesting process, the pitchers are cut at the base of the plant, leaving the rhizome. The pitchers may be cleaned such that all detritus and dirt are removed, and assayed for bacterial content (such assays are well known to one of ordinary skill in the art). During the chopping process, the pitchers may be cut lengthwise and/or chopped into strips (e.g., about 1 to 2.5 inch strips). In some embodiments, during the chopping process, the strips may be placed in a blender/chopper.

The chopped plant material may be placed in a jar or container, e.g., a glass jar. Any appropriate container may be used, for example a glass jar. Clear jars may be used as well as other shaded containers such as amber glass jars. Liquid is added to the chopped plant material, e.g., at a ratio of about 1 gram chopped plant material to about 2 mL liquid. The liquid may be, for example, an alcohol blend. In some embodiments, the liquid comprises an alcohol and water, e.g., distilled water. For example, the alcohol may be grain alcohol such as Everclear.

The liquid has a ratio of alcohol to water. In some embodiments, the ratio is about 60:40 alcohol to water. In some embodiments, the ratio is about 50:50 alcohol to water. In other embodiments, the ratio is about 40:60 alcohol to water. In still other embodiments, the ratio is about 30:70 alcohol to water. In some embodiments, the ratio is about 20:80 alcohol to water. In other embodiments, the ratio is about 10:90 alcohol to water. In still other embodiments, the ratio is about 70:30 alcohol to water. In some embodiments, the ratio is about 80:20 alcohol to water. In other embodiments, the ratio is about 90:10 alcohol to water. As an example, in some embodiments, about 454 grams of chopped plant material is placed in a jar, and about 908 mL of the liquid (with about a 60/40 ratio of alcohol (Everclear) to distilled water) is added to the chopped plant material.

After the liquid is added to the chopped plant material, the container is sealed. In some embodiments, the mixture is allowed to incubate for an incubation period, e.g., between about 1 to 2 days, between about 2 to 7 days, between about 1 to 2 weeks, between about 2 to 3 weeks, between about 4 to 6 weeks, more than 6 weeks, etc. In some embodiments, the mixtures are stirred occasionally during the incubation period. The incubation period, or a portion of the incubation period may feature placing the container in a low-light or dark environment.

After the incubation period, the liquid is decanted off, e.g., with a coffee filter or vacuum. The resultant liquid is the pitcher plant tincture, which may be stored and sealed, e.g., in amber glass bottles.

The following is a non-limiting example of making a *Sarracenia* tincture:
1. Cut the *Sarracenia* pitcher plants lengthwise and then chop into 1-2½ inch strips.
2. Blend the plant material with a small amount of liquid. The liquid is about a 60/40% blend of Everclear to distilled water.
3. Place the chopped herbs in glass jars in a quantity of about 454 grams.
4. Measure about 908 mL of a liquid of about 60/40% Everclear to distilled water and poured over the chopped plant material.
5. Seal the jars and let sit for about 4 to 6 weeks in a dark room.
6. Occasionally stir the jars.
7. After the plant material has sat for about 4 to 6 weeks, the liquid is decanted off with a coffee filter or vacuum.
8. The resultant liquid is stored in amber glass bottles and sealed.

Pitcher Plant Infused Solution

In some embodiments, a *Sarracenia* infused solution is made from a *Sarracenia* tincture. The *Sarracenia* tincture is mixed with a solvent and distilled for a period of time to remove the alcohol. In some embodiments, distilling the *Sarracenia* tincture and solvent mixture infuses the solvent with the *Sarracenia* component. In some embodiments, the solvent is oil or glycerin. In some embodiments, the oil is a carrier oil such as castor oil and coconut oil. When using oil as a solvent, the resulting solution is a *Sarracenia* infused oil.

In some embodiments, the ratio of *Sarracenia* tincture to solvent is between about 30:70 to 60:40. In other embodiments, the ratio of *Sarracenia* tincture to solvent is between about 30:70 to 40:60. In still other embodiments, the ratio of *Sarracenia* tincture to solvent is between about 40:60 to 50:50. In some embodiments, the ratio of *Sarracenia* tincture to solvent is between about 50:50 to 60:40. In other embodiments, the alcohol in the tincture is grain alcohol, such as Everclear.

In one embodiment, distilling the *Sarracenia* tincture and solvent mixture comprises placing the *Sarracenia* tincture and solvent mixture in a storage container; capping the storage container with a cap having at least one aperture and at least one tube, placing a tube second end in a collection container; heating the *Sarracenia* tincture and solvent mixture to a temperature at about a boiling point of the alcohol to vaporize the alcohol; and collecting the alcohol vapors in the collection container. In some embodiments, the period of time for distilling the *Sarracenia* tincture and solvent mixture is between about 1 to 3 hours, such as 1-2 or 2-3 hours.

The temperature of distillation can be about 75° C. and 90° C., such as about 75° C. and 80° C., 80° C. and 85° C., or 85° C. and 90° C. In some embodiments, a heat source for the distillation process is a hot plate, a stove, or a burner.

The following is a non-limiting example of making a *Sarracenia* infused solution:

1. Measure about 500 mL of *Sarracenia* spp. tincture
2. Measure about 500 mL of solvent
3. Pour both into an Erlenmeyer flask.
4. Top the flask with a rubber stopper that has tubing coming out of the stopper and into a large glass collection container.
5. Place the flask on a heat source, such as a hot plate.
6. Heat the flask containing the mixture on low or low-medium heat for about 1-2 hours and monitor flask. As it heats, the alcohol in the *Sarracenia* spp. tincture will evaporate off and could blow off the rubber stopper if the pressure inside the flask exceeds the evaporation. If this is the case, then lower the heat.
7. After about 1-2 hours, the alcohol will be evaporated off and the oil or liquid base will be completely infused with the healing properties of the carnivorous plant.

Formulations and Methods of Treatment

The present invention features a treatment designed to stimulate a healing response/cascade to circulating levels of inflammation by increasing fibroblast growth factor levels while simultaneously bringing fibrinogen levels to homeostatic levels, therefore alleviating patient symptoms related to pain and inflammation. As used herein, said treatment is referred to as "Cytenssic therapy", in which Cytenssic means "cell essence". This therapy utilizes various combinations of formulations that synergize the pitcher plant extracts, or other carnivorous plants herein, with known antioxidants, anti-inflammatory herbals, bases, injectables, nutraceuticals (supplements) or mixtures thereof. The mode of administration to the patient may be selected by a physician of ordinary skill in the art.

Figure 2:
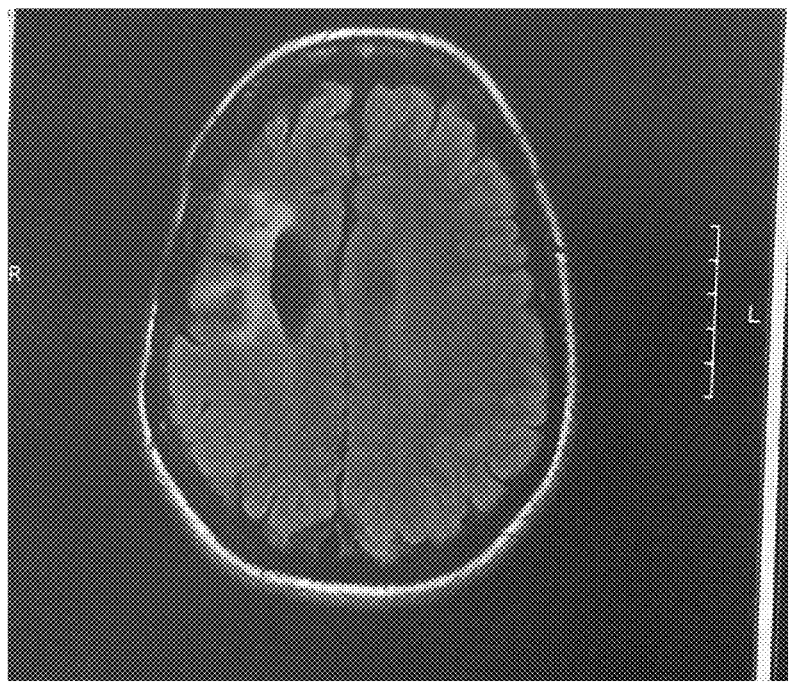
FIG. 2 shows MRI images of the same brain taken three months later. The patient was administered spinal injections the composition of the present invention during those three months.

Referring now to FIGS. 1-2, according to one embodiment, the present invention features a method of treating inflammation in a subject. The method may comprise administering one or more injections of a therapeutically effective amount of a composition to fascia and ligaments surrounding a spine of the subject. Preferably, the one or more injections may be administered at a depth of about ½ inch into the skin. For example, the one or more injections of the composition may be administered into the Du Meridian acupuncture points, du14-2, using a 30 g, ½ inch needle. In preferred embodiments, the composition may comprise an herbal preparation of a carnivorous plant, and a glutathione. In one embodiment, the herbal preparation is at a range of about 0.1% to 99% volume of the composition. In another embodiment, the glutathione is at a range of about 0.1% to 99% volume of the composition. Without wishing to limit the invention to a particular theory or mechanism, the herbal preparation of the carnivorous plant is effective for facilitating transmission of the glutathione to fibroblast growth factors. Moreover, the administering of the composition to the subject can increase fibroblast growth factors at measureable levels in the subject, and adjusts fibrinogen levels to homeostatic levels in the subject, thereby ameliorating symptoms of the inflammation of the subject. Furthermore, the injections may be effective for stimulating movement of fibroblast cells. When utilizing the method described herein, after administering the injections, the fibroblast growth factors increases to high levels until healing is accomplished. When the treatment is complete, the FGF levels then decrease to FGF homeostatic levels in the 100-199 Ru/mL range.

In some embodiments, the herbal preparation of the carnivorous plant is prepared from a pitcher plant, such as *Sarracenia purpurea*. However, it is understood that any carnivorous plant may be used for the herbal preparation.

In other embodiments, the composition may be administered at a dosage of about 8 to 20 cc every 4 weeks. For example, the composition may be administered at about 9 cc, depending on the tolerance of the subject, and then increased at each subsequent dosage.

In one embodiment, the composition may further comprise one or more supplements, at a range of about 0.1-99% vol of the composition, selected from a group consisting of vitamins, minerals, essential fatty acids, amino acids, and amine derivatives. The herbal preparation of the carnivorous plant may be effective for facilitating transmission of the one or more supplements to the fibroblast growth factors. Examples of vitamins include, but are not limited to, retinoic acid (Vitamin A), vitamin B-complex, vitamin C, vitamin D, vitamin E, and vitamin K. Examples of minerals include, but are not limited to, calcium, phosphorus, magnesium, sodium, potassium, chloride, sulfur, iron, manganese, copper, iodine, zinc, cobalt, fluoride and selenium. In some embodiments, the amine derivative may be glucosamine. In other embodiments, the amino acid may be cysteine or arginine, such as L-arginine.

In a preferred embodiment, the supplement is magnesium and salts thereof. Without wishing to limit the present invention to a particular theory or mechanism, when the subject has low levels of magnesium, symptoms of the subject's disorder can flare. By increasing magnesium levels, the symptoms decrease and the subject starts to heal. For example, the composition in combination with magnesium chloride may be administered to the subject by injection into or at the spine to increase magnesium levels, thereby alleviating muscle pain, twitching, and spasms. In addition, the presence of pain can signal that the subject has low levels of glutathione and/or magnesium. Hence, by correcting the glutathione and/or magnesium levels, the subject can experience pain relief.

In yet another embodiment, the composition may further comprise a thyroid hormone. For example, the composition in combination with thyroid hormone at a range of about 0.1-99% vol of the composition, i.e. about 5-15% vol of the composition, may be administered to the subject by injection into or at the spine.

According to an exemplary embodiment, the composition may comprise the herbal preparation of *Sarracenia purpurea* at a range of about 0.1-99% vol of the composition, glutathione at a range of about 0.1-99% vol of the composition, magnesium at a range of about 0.1-99% vol of the composition, vitamin A at a range of about 0.1-99% vol of the composition, vitamin D at a range of about 0.1-99% vol of the composition, L-arginine at a range of about 1-99% vol of the composition, glucosamine at a range of about 0.1-99% vol of the composition, and a thyroid hormone at a range of about 0.1-99% vol of the composition.

In some embodiments, the composition may further comprise one or more of the following: aloe vera gel, glycerine, natural oils, an emulsifier, menthol crystals, berries, green tea extract, medicinal mushrooms, turmeric, ginger, viscum, burdock, devil's claw, boneset, valerian, skullcap, marshmallow root, mullein leaf, elecampane root, fennel seed, licorice root, old man's beard lichen, orange peel, osha root, wild cherry bark, propolis, ginkgo, poppy, polygonum, hops, passionflower, avena, and arnica.

In other embodiments, the composition may further comprise a therapeutically effective amount of one or more plant preparations selected from a group consisting of an astragalus preparation, a curcumin preparation, a black cohosh preparation, an *Orchidaceae* plant preparation, a *Lilium* plant preparation, a *Sanguinaria canadensis* preparation, and a berry preparation. The berry preparation may be an antioxidant. The *Orchidaceae* plant preparation may be a fibroblast protector. The *Lilium* plant preparation may be a fibroblast motility enhancer.

In still other embodiments, the composition may further comprise one or more solutions selected from a group consisting of a witch hazel solution, a lye solution, a salt solution, coconut oil, a dimethyl sulfate (DMSO) solution, and a gelatin.

In further embodiments, the composition may further comprise one or both of an adrenal formulation and an immune formulation. In one embodiment, the adrenal formulation may comprise withania at about 30% vol of the adrenal formulation, rhodiola at about 25% vol of the adrenal formulation, licorice at about 15% vol of the adrenal formulation, milky oats at about 10% vol of the adrenal formulation, ginseng at about 10% vol of the adrenal formulation, gota kola at about 5% vol of the adrenal formulation, and lemon balm at about 5% vol of the adrenal formulation. In another embodiment, the immune formulation may comprise LIVIXIR at about 30% vol of the immune formulation, astragalus at about 15% vol of the immune formulation, elderberry at about 10% vol of the immune formulation, hydrastis at about 10% vol of the immune formulation, echinacea at about 10% vol of the immune formulation, usnea at about 5% vol of the immune formulation, and inula at about 5% vol of the immune formulation.

In some embodiments, Cytenssic therapy may involve the administration of a series of injections to the joint space, tendon, ligament, or muscle. A systemic effect is seen when a pitcher plant injectable is mixed with glutathione for injection into the spinal area, and placed via needle manipulation in the tissue to be affected, such as a ligament, tendon, or any other kind of connective tissue surrounding the spine. For example, when the needle is placed at or near the joint space, it can affect healing as shown by a reduction in local scar tissue and pain responses. Systemic effects may be noted by a patient's reaction such as hot flashes, chills, low-grade fever, or mineral salt cravings within a short time period after receiving injections if nutrient levels in the extra-cellular matrix are low.

Glutathione is a known antioxidant, but it also has residence on two cysteine residues within fibroblast growth factors, in particular FGF-2 (Mueller and Fusenig 2011). The invention shows that modulation of FGF activity is glutathione dependent, as low levels of glutathione prevent a healing response that is permanent. Therefore, the synergetic effects of pitcher plant and glutathione are needed for Cytenssic therapy injections.

Transdermal Effect

In other embodiments, Cytenssic therapy involves the pitcher plant combined with any topical agent designed to soothe or heal the skin from inflammatory, arthritic or cancerous conditions. Inflammatory healing reactions involve the transformation of fibroblasts into myofibroblasts. The myofibroblasts use a high amount of the fibrin from fibrinogen, and are only active for acute conditions. However, if the inflammation continues for long periods of time, myofibroblasts stay in the area, which is commonly the case for cancerous tumors and metastasis (Mueller and Fusenig 2011).

According to another embodiment, the present invention features a topical composition comprising an herbal preparation of a pitcher plant. In one embodiment, the herbal preparation of the pitcher plant is at a range of about 1% to 99% volume of the composition. The composition may be effective in reducing inflammation and stimulating movement and activity of fibroblasts. In some embodiments, the topical formulation may be in prepared as a viscous emulsion, such as a lotion, cream, oil, balm or gel. In preferred embodiments, the pitcher plant is a *Sarracenia flava* plant. *Sarracenia flava* is supposedly toxic since it contains the neurotoxin, coniine. However, the present invention has discovered that topically administration of the *Sarracenia flava* preparation to mammals can induce healing effects.

In some embodiments, the topical composition may further comprise glutathione at a range of about 0.1-99% vol of the topical composition. In other embodiments, the topical formulation may further comprise one or more of the following: aloe vera gel, glycerine, natural oils, an emulsifier, menthol crystals, berries, green tea extract, medicinal mushrooms, turmeric, ginger, viscum, burdock, devil's claw, boneset, valerian, skullcap, marshmallow root, mullein leaf, elecampane root, fennel seed, licorice root, old man's beard lichen, orange peel, osha root, wild cherry bark, propolis, ginkgo, poppy, polygonum, hops, passionflower, avena, and arnica.

In other embodiments, the topical composition may further comprise a therapeutically effective amount of one or more plant preparations, at a range of about 0.1-99% vol of the topical composition, selected from a group consisting of an astragalus preparation, a curcumin preparation, a black cohosh preparation, an Orchidaceae plant preparation, a *Lilium* plant preparation, a *Sanguinaria canadensis* preparation, and a berry preparation. The berry preparation may be an antioxidant. The Orchidaceae plant preparation may be a fibroblast protector. The *Lilium* plant preparation may be a fibroblast motility enhancer.

In still other embodiments, the topical composition may further comprise one or more solutions, at a range of about 0.1-99% vol of the topical composition, selected from a group consisting of a witch hazel solution for astringing the tissues, clay for drawing out toxins, a lye solution for producing soap products for additional cleansing, a salt solution such as epsom salts for mineral balance, a dimethyl sulfate (DMSO) solution for additional absorptive benefits, coconut oil, and a gelatin.

In yet other embodiments, the topical formulation may further comprise one or more supplements, at a range of about 0.1-99% vol of the topical composition, selected from a group consisting of vitamins, minerals, essential fatty acids, amino acids, and amine derivatives. The vitamins may be selected from a group consisting of retinoic acid, vitamin B-complex, vitamin C, vitamin D, vitamin E, and vitamin K. The minerals may be selected from a group consisting of calcium, phosphorus, magnesium, sodium, potassium, chloride, sulfur, iron, manganese, copper, iodine, zinc, cobalt, fluoride and selenium. The amine derivative may be glucosamine. The amino acid may be cysteine or arginine.

Without wishing to limit the invention to a particular theory or mechanism, it has been surprisingly discovered that when applied topically, the herbal preparation of the pitcher plant creates a transdermal effect, i.e. the herbal preparation of the pitcher plant can deliver substances across and through the skin. For instance, magnesium is a mineral that is typically insoluble in fats. When magnesium was combined with the herbal preparation of the pitcher plant, specifically a pitcher plant infused oil, magnesium was able to dissolve in the herbal preparation of the pitcher plant. Hence, substances, such as minerals, vitamins, and others that are insoluble in fats, can be administered topically via the herbal preparation of the pitcher plant. For example, when the herbal preparation of the pitcher plant, in combination with vitamins and minerals, is administered topically on the subject's skin, the subject will then taste the vitamins and minerals in his or her mouth because the pitcher plant transports the vitamins and minerals through the skin and to the fibroblasts, which are stimulated into movement by the pitcher plant.

Oral Administration

Likewise, oral administration may be implemented for internal support. According to one embodiment, the present invention features an oral composition comprising an herbal preparation of a pitcher plant. In one embodiment, the herbal preparation is a pitcher plant tincture having an alcohol to water volumetric ratio of about 50:50 to 60:40. Preferably, the pitcher plant is a *Sarracenia purpurea* plant. The oral composition may be effective for decreasing fibrinogen levels.

In alternative embodiments, the oral composition may further comprise herbs such as orchids for anti-senescence fibroblastic support or lily extracts for enhanced fibroblast motility. Oral administration of the composition may also be anti-inflammatory when the pitcher plant is combined with herbs such as curcumin or black cohosh. Astragalus may be combined with the pitcher plant for cytoprotective effects, or berries for additional antioxidant effects. In preferred embodiments, the oral composition may be administered to the subject at a dose of about 1-2 tsp per day or 1 Tbsp per day for two months in order to decrease fibrinogen to homeostatic levels.

Drop Therapy

In alternative embodiments, the herbal preparation of the pitcher plant may be used in acupuncture. The acupuncture needle is dipped in the herbal preparation of the pitcher plant, and if desired, with another tincture/essential oil, before using the needle in the acupuncture process. This treatment is known as drop therapy. Non-limiting examples of essential oils include turmeric, mint, rosemary, cinnamon, frankincense, and basil. For example, patients with sinus infections will clear the infection better with the drop therapy than just acupuncture alone. Without wishing to limit the invention to a particular theory or mechanism, the pitcher plant act can decrease fibrinogen levels to homeostatic levels locally around the insertion site of the acupuncture needle. In addition, fibroblast movement activity and movement is stimulated. In other embodiments, when administering the composition via injection, the injection needle may be dipped in the herbal preparation of the pitcher plant, and if desired, with another tincture/essential oil, prior to injecting the needle. In further embodiments, drop therapy can feature sublingually administering the herbal preparation of the pitcher plant, and if desired, with another tincture/essential oil.

Burnables

In an alternative embodiment, the pitcher plant may be used in candles and incense. The dried pitcher plant material or the pitcher plant preparation may be used in the candles or incense. For example, a pitcher plant tincture may be immersed into wax such as soy or beeswax. Alternatively, the wax can be infused with the pitcher plant component.

In another alternative embodiment, the pitcher plant may be smoked by a subject. Smoking of the pitcher plant may be effective for instilling a mild, relaxing mood in the subject. In one embodiment, the dried plant material of the pitcher plant may be smoked directly. In another embodiment, a pitcher plant infused oil may be used in a vaporizing device. Without wishing to limit the invention to a particular theory or mechanism, a limonene component and/or a cannabinoid component of the pitcher plant can induce an anxiolytic effect in the subject.

In some embodiments, any of the aforementioned compositions may also treat insomnia. The compositions may affect how a person sleeps through the night since it is well-documented that the cytokine Interleukin 6 (IL-6), which can stimulate inflammatory and auto-immune processes in many diseases, is active in people with insomnia. As a non-limiting example, a formula with herbs may contain black cohosh or other herbs that lower IL-6 to obtain anti-insomnia properties.

EXAMPLES

The following are non-limiting examples of the present invention.

Example 1

Oral Administration

1. A patient is prescribed to take an oral formulation of an herbal preparation of the pitcher plant, at a dosage of 1 Tbsp, twice/day, for 3 weeks.
2. Re-test fibrinogen levels.
3. Depending on fibrinogen levels, the patient is prescribed a maintenance dose of ½ to 1 Tbsp/day until fibrinogen levels decrease to normal levels.

Example 2

Administration by Injection

1. Draw patient FGF-23 labs.
2. Perform spinal injections of 75/25% pitcher plant to glutathione. Use a 30 g ½ inch needle applied right below the spinous processes, into the Du meridian acupuncture points, du14-2. The physician can inject at all points or at key points such as 14, 11, 10, 6, 4 and 2, depending on how much scar tissue it felt by the physician and how much injected fluid can be tolerated by the patient. The physician can start with 9 cc total and at other visits, may go up to 18 cc along the spine.
3. Do monthly injections, ideally every 4 weeks, to allow for time to heal between and see the symptoms change.
4. Check the FGF-23 levels at intervals decided by the physician and patient.

Example 3

A 39-year old female patient was suffering from fatigue. The physician prescribed a topical cream of vitamins and the herbal preparation of the pitcher plant. The patient reported that she applied the topical cream on her abdomen. Within a few hours, she got flushed as though she took orally a large dose of multi-vitamins or B-complex. The patient reported that she has great energy after taking the topical cream.

Example 4

A female patient suffers from fibromyalgia. Pre-labs of the patient reported a fibrinogen activity of 326 mg/dL. The patient smokes 1 pack of cigarettes per day. Smoking is known to increase fibrinogen. The physician prescribed 1 Tbsp, twice/day of *S. purpurea* tincture 60/40. The patient continued to smoke cigarettes while taking the tincture. Post-labs taken 11 days later reported that the fibrinogen activity decreased to 261 mg/dL.

Example 5

Pre-labs of a male patient shows a fibrinogen activity of 366 mg/dL. Thirty-nine days later, the patient ate copious amount of sugary foods during the holidays, and increased his fibrinogen activity to 404 mg/dL. Sugar is known to increase fibrinogen. Two months later, the patient was suffering from painful irritable bowel syndrome. His abdominal inflammation is further aggravated by eating sugar. His fibrinogen activity increased to 418 mg/dL. His physician prescribed a dose of 1 Tbsp, twice/day of the pitcher plant tincture. Forty days later, the patient reported that his abdominal pain decreased significantly, as did the fibrinogen. His post-lab fibrinogen activity decreased to 357 mg/dL.

Example 6

A 50-year old female has the genes for cervical cancer. The patient's PAP test results reported: "Atypical squamous cells of undetermined significance, favor low grade lesion. This latter would correspond to mild dysplasia and/or HPV effect." The patient's physician prescribed a vaginal cream of the topical composition to be applied nightly, unless the patient was menstruating. Seven months later, a second PAP test of the patient reported: "Negative for intraepithelial lesion or malignancy. Benign cellular changes with reactive features." The patient no longer has precancerous cells.

Example 7

A female patient suffered from the starting phases of dementia, osteoarthritis, fibromyalgia and IBS. Pre-labs of the patient reported an FGF-23 level of 99 Ru/mL. The FGF-23 level indicates that the patient is a slow-healer. The patient's physician prescribed a series of injections of the composition at varying ratios, usually 75/25% pitcher plant to glutathione. Labs taken 4 months later reported an increase in FGF-23 levels to 534 Ru/mL. The patient reported that her memory was returning and that she no longer suffered from fibromyalgia and IBS pain. Furthermore, her osteoarthritis was also diminishing.

As used herein, the term "about" refers to plus or minus 10% of the referenced number.

Various modifications of the invention, in addition to those described herein, will be apparent to those skilled in the art from the foregoing description. Such modifications are also intended to fall within the scope of the invention. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures.

In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed:
1. A method of treating inflammation in a subject, said method comprising administering one or more injections of a therapeutically effective amount of a composition into ligaments and fascia surrounding a spine of the subject, wherein the composition comprises:
   a. an herbal preparation of a carnivorous plant, wherein the herbal preparation is at a range of about 0.1% to 99% volume of the composition; and
   b. glutathione, wherein glutathione is at a range of about 0.1% to 99% volume of the composition;
   wherein the herbal preparation of the carnivorous plant is effective for facilitating transmission of glutathione to fibroblast growth factors, and
   wherein the administering of the composition to the subject is effective for increasing fibroblast growth factors at measureable levels in the subject, and adjusting fibrinogen levels to homeostatic levels in the subject, thereby ameliorating symptoms of and reducing inflammation in the subject.

2. The method of claim 1, wherein the herbal preparation of the carnivorous plant is prepared from a pitcher plant.

3. The method of claim 1, wherein the one or more injections is effective for stimulating movement of fibroblast cells.

4. The method of claim 1, wherein the composition is administered at a dosage of about 8 to 20 cc every 4 weeks.

5. The method of claim 1, wherein the one or more injections is administered into ligaments and fascia surrounding the spine at a depth of about ½ inch.

6. The method of claim 1, wherein the composition further comprises one or more supplements selected from a group consisting of vitamins, minerals, essential fatty acids, amino acids, and amine derivatives, wherein the herbal preparation of the carnivorous plant is effective for facilitating transmission of the one or more supplements to the fibroblast growth factors.

7. The method of claim 1, wherein the composition further comprises vitamins, wherein the vitamins are selected from a group consisting of vitamin A, vitamin B-complex, vitamin C, vitamin D, vitamin E, and vitamin K.

8. The method of claim 1, wherein the composition further comprises minerals, wherein the minerals are selected from a group consisting of calcium, phosphorus, magnesium, sodium, potassium, chloride, sulfur, iron, manganese, copper, iodine, zinc, cobalt, fluoride and selenium.

9. The method of claim 1, wherein the composition further comprises an amine derivative, wherein the amine derivative is glucosamine.

10. The method of claim 1, wherein the composition further comprises an amino acid, wherein the amino acid is cysteine or arginine.

11. The method of claim 1, wherein the composition further comprises a thyroid hormone.

12. The method of claim 1, wherein the composition further comprises magnesium at a range of about 1-99% vol of the composition, vitamin A at a range of about 1-99% vol of the composition, vitamin D at a range of about 1-99% vol of the composition, L-arginine at a range of about 1-99% vol of the composition, glucosamine at a range of about 1-99% vol of the composition, and a thyroid hormone at a range of about 1-99% vol of the composition.

* * * * *